(12) United States Patent
Yamamura et al.

(10) Patent No.: US 10,765,094 B2
(45) Date of Patent: Sep. 8, 2020

(54) INFLAMMATION REPORTER SYSTEM

(71) Applicants: TRANSGENIC INC., Fukuoka-shi, Fukuoka (JP); NATIONAL UNIVERSITY CORPORATION KUMAMOTO UNIVERSITY, Kumamoto-shi, Kumamoto (JP); NATIONAL UNIVERSITY CORPORATION GUNMA UNIVERSITY, Maebashi-shi, Gunma (JP)

(72) Inventors: Kenichi Yamamura, Kumamoto (JP); Takao Iwawaki, Gunma (JP); Daisuke Oikawa, Gunma (JP); Tomoo Ishikawa, Hyogo (JP)

(73) Assignees: TRANSGENIC INC., Fukuoka-Shi (JP); NATIONAL UNIVERSITY CORPORATION KUMAMOTO UNIVERSITY, Kumamoto-Shi (JP); NATIONAL UNIVERSITY CORPORATION GUNMA UNIVERSITY, Maebashi-Shi (JP)

( * ) Notice: Subject to any disclaimer, the term of this patent is extended or adjusted under 35 U.S.C. 154(b) by 0 days.

(21) Appl. No.: 15/329,477

(22) PCT Filed: Jul. 31, 2014

(86) PCT No.: PCT/JP2014/070798
§ 371 (c)(1),
(2) Date: Jan. 26, 2017

(87) PCT Pub. No.: WO2016/017039
PCT Pub. Date: Feb. 4, 2016

(65) Prior Publication Data
US 2017/0215394 A1 Aug. 3, 2017

(51) Int. Cl.
*C07H 21/04* (2006.01)
*A01K 67/00* (2006.01)
*C12Q 1/00* (2006.01)
*C12N 15/63* (2006.01)
*A01K 67/027* (2006.01)
*C12N 15/09* (2006.01)
*A61K 49/00* (2006.01)
*A61K 31/70* (2006.01)

(52) U.S. Cl.
CPC ........ *A01K 67/0278* (2013.01); *A01K 67/027* (2013.01); *A61K 49/0008* (2013.01); *C12N 15/09* (2013.01); *A01K 2217/052* (2013.01); *A01K 2227/105* (2013.01); *A01K 2267/0368* (2013.01)

(58) Field of Classification Search
CPC .......... A01K 67/0278; A01K 2217/052; A01K 2227/105; A01K 2267/0368; A01K 67/027; C12N 15/09; A61K 49/0008
See application file for complete search history.

(56) References Cited

U.S. PATENT DOCUMENTS 6,331,613 B1 * 12/2001 Dumoutier ............. C07K 14/52
435/252.3
2004/0146987 A1 * 7/2004 Zdanovsky .......... C12Q 1/6897
435/69.7
2010/0297620 A1 * 11/2010 Umezawa et al.
2013/0298263 A1 11/2013 Iwawaki et al.
2014/0308675 A1 10/2014 Mizota et al.

FOREIGN PATENT DOCUMENTS

| JP | 9-500533 A | 1/1997 |
| JP | 2007-209227 A | 8/2007 |
| JP | 4446057 B2 | 4/2010 |
| WO | WO 95/03397 A1 | 2/1995 |
| WO | WO 99/37142 A1 | 7/1999 |
| WO | WO 2012/099279 A1 | 7/2012 |
| WO | WO 2013/054846 A1 | 4/2013 |

OTHER PUBLICATIONS

Denes et al. Caspase-1: is IL-1 just the tip of the ICEberg? Cell death and disease 3, e338:doi:10.1038/cddis.2012.86, 9 pages, (Year: 2012).*
Agard et al. Inflammatory stimuli regulate caspase substrate profiles. Molecular & Cellular Proteomics 9:880-893, (Year: 2010).*
Naldiri et al. The inflammatory caspases: key players in the host response to pathogenic invasion and sepsis. J. Immunology 177: 4239-4245, (Year: 2006).*
Ghayur et al. Caspase-1 processes IFN-gamma-inducing factor and regulates LPS-induced IFN-gamma production. Nature 386: 619-623, (Year: 1997).*
Bartok et al., "iGLuc: a luciferase-based inflammasome and protease activity reporter," Nat. Methods (Feb. 2013), vol. 10, No. 2, pp. 147-154.
Croxford, A. L. and T. Buch, "Cytokine reporter mice in immunological research: perspectives and lessons learned," Immunology (2010), vol. 132, pp. 1-8.

(Continued)

*Primary Examiner* — Quang Nguyen
(74) *Attorney, Agent, or Firm* — Birch, Stewart, Kolasch & Birch, LLP

(57) ABSTRACT

The present invention provides a method for detection of an inflammatory reaction, which comprises using a transformant or transgenic non-human animal transfected with a vector comprising a promoter for a gene encoding an inflammatory cytokine, a gene encoding a reporter protein, a gene encoding the inflammatory cytokine, and a gene encoding a proteolytic signal sequence to thereby detect an inflammatory reaction induced upon inflammatory stimulation in the transformant or in the transgenic non-human animal.

11 Claims, 8 Drawing Sheets
(4 of 8 Drawing Sheet(s) Filed in Color)
Specification includes a Sequence Listing.

(56) References Cited

OTHER PUBLICATIONS

International Search Report dated Nov. 11, 2014, in PCT International Application No. PCT/JP2014/070798.
Iwawaki et al., "A transgenic mouse model for monitoring endoplasmic reticulum stress," Nature Medicine (Jan. 2004), vol. 10, No. 1, pp. 98-102, plus Supplementary Fig. 1.
Li et al., "Bioluminescence imaging for IL-1β expression in experimental colitis," Journal of Inflammation (2013), vol. 10, No. 16, pp. 1-6.
Li et al., "Functional Imaging of interleukin 1 beta expression in inflammatory process using bioluminescence imaging in transgenic mice," BMC Immunology (2008), vol. 9, No. 49, pp. 1-9.
Matsushima et al., "Intravital Imaging of IL-1β Production in Skin," Journal of Investigative Dermatology (2010), vol. 130, pp. 1571-1580.
Oikawa et al., "A transgenic mouse model for monitoring oxidative stress," Scientific Reports (Jan. 19, 2012), vol. 2, No. 229, pp. 1-8.
Iwawaki et al., "Transgenic mouse model for imaging of interleukin-1β-related inflammation in vivo," Scientific Reports, vol. 5, No. 1, Dec. 2015 (Published Nov. 24, 2015), pp. 1-10, XP055428772.

* cited by examiner

INFLAMMATION REPORTER SYSTEM

TECHNICAL FIELD

The present invention relates to a method for detection of an inflammatory reaction.

BACKGROUND ART

Inflammatory reaction is one of the body's responses deeply involved in the symptoms of many diseases, and is now an important subject of study in understanding their pathology and/or in developing therapeutic strategies against these diseases. For this reason, it is indispensable to develop a technique which allows detection of the actual conditions of inflammation.

A typical inflammatory reaction has been elucidated to occur through the following mechanism. Namely, once a source of infection (e.g., bacteria, viruses) has entered the body, the source of infection will be detected by cell surface receptors, followed by induction of cytokine secretion. The secreted cytokines will serve as guides to cause immunocytes (e.g., macrophages) to migrate to the infection site, whereby the source of infection will be eliminated. The increased activity of these immunocytes during elimination will result in flare, fervescence, pain and swelling which are characteristic of inflammation.

As a cytokine which is significantly involved in this inflammatory reaction and also receives attention as an inflammatory marker, interleukin-1 beta (IL-1β) has been known. IL-1β is not substantially secreted in the absence of inflammatory stimulation, but is known to be produced and secreted at a very high level in each tissue upon inflammatory stimulation (FIG. 1).

IL-1β has been found to be strictly regulated by the following characteristic two-stage control. The gene expression of IL-1β is activated by transcription factor NF-κB induced during inflammatory reaction, and the activated IL-1β gene expression in turn promotes the production of precursor proIL-1β. Then, proIL-1β will be cleaved by caspase activated in inflammasomes and converted into secretable mature IL-1β (FIG. 2).

Some reports have been issued about the monitoring of IL-1β gene expression in which luciferase or red fluorescent protein is used as a reporter molecule (Non-patent Documents 1 and 2). In these reports, it is shown that transgenic mice carrying a reporter molecule are prepared and in this inflammation model, reporter signals can be detected and also can be used for in vivo imaging analysis. However, this method relies only on transcriptional regulation, which is one factor contributing to a cascade of inflammatory reactions, and hence this method is insufficient to monitor physiological inflammatory reactions.

On the other hand, a reporter system regulated by inflammasomes has also been reported (Non-patent Document 3). In this report, a reporter molecule is design such that it is in an inactive state due to aggregation in the absence of inflammation, but it will be converted into a monomer form to exert its activity when inflammasomes become functional upon inflammatory stimulation. However, this system also relies only on inflammasomes and is therefore insufficient in sensitivity. Moreover, this system has not been verified as to whether it is functional in living mice.

Other attempts have also been made to induce protein expression by various internal or external stimuli (e.g., oxidative stress, endoplasmic reticulum stress) and to visualize the event taking place (Patent Documents 1 and 2, Non-patent Documents 4 and 5).

PRIOR ART DOCUMENTS

Patent Documents

Patent Document 1: WO2012/099279
Patent Document 2: Japanese Patent No. 4446057

Non-Patent Documents

Non-patent Document 1: Li L. et al "Functional imaging of interleukin 1 beta expression in inflammatory process using bioluminescence imaging in transgenic mice" BMC Immunol., vol. 9, 49 (2008)
Non-patent Document 2: Matsushima H. et al "Intravital imaging of IL-1 beta production in skin" J. Invest. Dermatol., vol. 130, 1571-1580 (2010)
Non-patent Document 3: Bartok E. et al "iGLuc: a luciferase-based inflammasome and protease activity reporter" Nat. Methods., vol. 10, 147-154 (2013)
Non-patent Document 4: Scientific Reports 2012; 2:229. Epub 2012 Jan. 19.
Non-patent Document 5: Nature Medicine 10, 98102 (1 Jan. 2004)

SUMMARY OF THE INVENTION

Problem to be Solved by the Invention

The present invention aims to provide a technique which allows highly efficient and highly sensitive detection and measurement of a local inflammatory reaction particularly in a microregion in the living body. The present invention also aims to provide a gene vector which allows easy use of this detection method, as well as a transgenic mouse transfected with the gene vector of this reporter system, which allows further use in in vivo research and development.

Means to Solve the Problem

As a result of repeating extensive and intensive efforts to solve the problems stated above, the inventors of the present invention have found that based on the mechanism of inflammatory reaction which is regulated in two stages by the IL-1β gene and inflammasomes, a reporter system can be constructed which allows highly efficient and highly sensitive monitoring of physiological inflammatory reactions. Thus, the inventors of the present invention have constructed this monitoring method and a gene vector provided with this method, as well as a transgenic mouse, thereby completing the present invention.

Namely, the present invention is as follows.

(1) A vector comprising a promoter for a gene encoding an inflammatory cytokine, a gene encoding a reporter protein, a gene encoding the inflammatory cytokine, and a gene encoding a proteolytic signal sequence.

(2) The vector according to (1) above, wherein the inflammatory cytokine is interleukin 1β.

(3) The vector according to (1) or (2) above, wherein the reporter protein is luciferase.

(4) The vector according to any one of (1) to (3) above, wherein the gene encoding the inflammatory cytokine comprises a polynucleotide sequence encoding a peptide recognizable by caspase.

(5) A transformant comprising the vector according to any one of (1) to (4) above.

(6) A transgenic non-human animal transfected with the vector according to any one of (1) to (4) above.

(7) The transgenic non-human animal according to (6) above, wherein the non-human animal is a mouse.

(8) The transformant according to (5) above or the transgenic non-human animal according to (6) or (7) above, wherein the reporter protein is detected as a luminescence signal upon inflammatory stimulation.

(9) A method for detection of an inflammatory reaction, which comprises using the transformant according to (5) above or the transgenic non-human animal according to any one of (6) to (8) above to detect an inflammatory reaction induced upon inflammatory stimulation in the transformant or in the transgenic non-human animal.

(10) The method according to (9) above, wherein the gene encoding the inflammatory cytokine is expressed by transcription factor NF-κB induced during inflammatory reaction.

(11) The method according to (9) or (10) above, wherein the reporter protein is detected as a luminescence signal upon inflammatory stimulation.

(12) A method for screening of anti-inflammatory substances, which comprises bringing the transformant according to (5) above or the transgenic non-human animal according to any one of (6) to (8) above into contact with candidate substances under inflammatory stimulation to select an anti-inflammatory substance on the basis of the presence or absence of an inflammatory reaction serving as an indicator.

(13) A kit for detection of an inflammatory reaction or for screening of anti-inflammatory substances, which comprises the transformant according to (5) above or the transgenic non-human animal according to any one of (6) to (8) above.

Effects of the Invention

The present invention provides a reporter system which allows highly efficient and highly sensitive monitoring of inflammatory reactions. The system of the present invention allows visualization of inflammatory reactions and achieves extremely high sensitivity and efficiency.

BRIEF DESCRIPTION OF THE DRAWINGS

The patent or application file contains at least one color drawing. Copies of this patent or patent application publication with color drawing will be provided by the USPTO upon request and payment of the necessary fee.

DESCRIPTION OF EMBODIMENTS

The present invention will be described in more detail below.

1. Vector and Others as Well as Detection Method

The vector used in the present invention comprises a fusion gene composed of multiple genes ligated together, and is designed to express a fusion protein composed of a reporter molecule, a caspase recognition sequence and a proteolytic signal sequence under the control of a promoter for a gene encoding an inflammatory cytokine.

In the context of the present invention, the term "inflammatory cytokine" refers to a cytokine which is produced from helper T cells, monocytes, macrophages, neutrophils, dendritic cells or other cells upon activation with an antigen (e.g., bacteria) and which activates macrophages or other cells of the immune system, vascular endothelial cells or osteoclasts. Examples of such an inflammatory cytokine include IL-1β, IL-6, IL-8, IL-12, IL-13, IL-17, IL-18, tumor necrosis factor (TNF) and so on. Genes encoding inflammatory cytokines are expressed by transcription factor NF-κB induced during inflammatory reaction.

In the present invention, genes encoding these inflammatory cytokines or partial sequences thereof may be used. Information is known about genes encoding the above inflammatory cytokines and promoters for these genes. Partial sequences may be of any length as long as they ensure responsiveness to inflammation, and their length and region may be determined on the basis of enhanced expression in response to inflammation and/or processing in response to inflammation, etc.

IL-1β: Accession No. NM_008361.3
IL-6: Accession No. NM_031168.1
IL-8: Accession No. NM_009140.2
IL-12: Accession No. NM_001159424.1
IL-13: Accession No. NM_008355.3
IL-17: Accession No. NM_010552.3
IL-18: Accession No. NM_008360.1
TNF: Accession No. NM_001278601.1
IL-1β promoter: Accession No. NC_000068.7
IL-6 promoter: Accession No. NC_000071.6
IL-8 promoter: Accession No. NC_000071.6
IL-12 promoter: Accession No. NC_000069.6
IL-13 promoter: Accession No. NC_000077.6
IL-17 promoter: Accession No. NC_000067.6
IL-18 promoter: Accession No. NC_000075.6
TNF promoter: Accession No. NC_000083.6

For convenience of explanation, IL-1β is taken as an example herein.

A reporter gene is ligated downstream of a promoter for the IL-1β gene, and a gene construct comprising, for example, a IL-1β partial sequence and a proteolytic signal sequence is prepared downstream of the reporter gene. A peptide linker encoded by the IL-1β partial sequence comprises a sequence recognizable by caspase (i.e., a caspase recognition sequence). Moreover, the peptide linker encoded by the IL-1β partial sequence is a region on which caspase (caspase-1) acts when activated in a protein complex called inflammasome, and this peptide linker is cleaved by the action of caspase.

Figure 1:
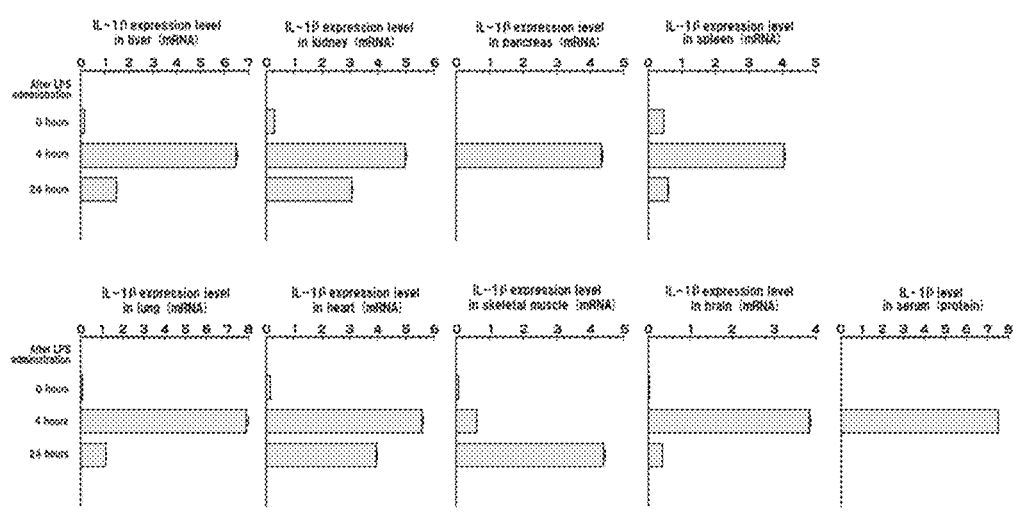
FIG. 1 shows changes in IL-1β levels after inflammatory stimulation with lipopolysaccharide (LPS). LPS used: SIGMA #L2654, concentration of use: 3 to 4 μg/g body weight
Figure 2:
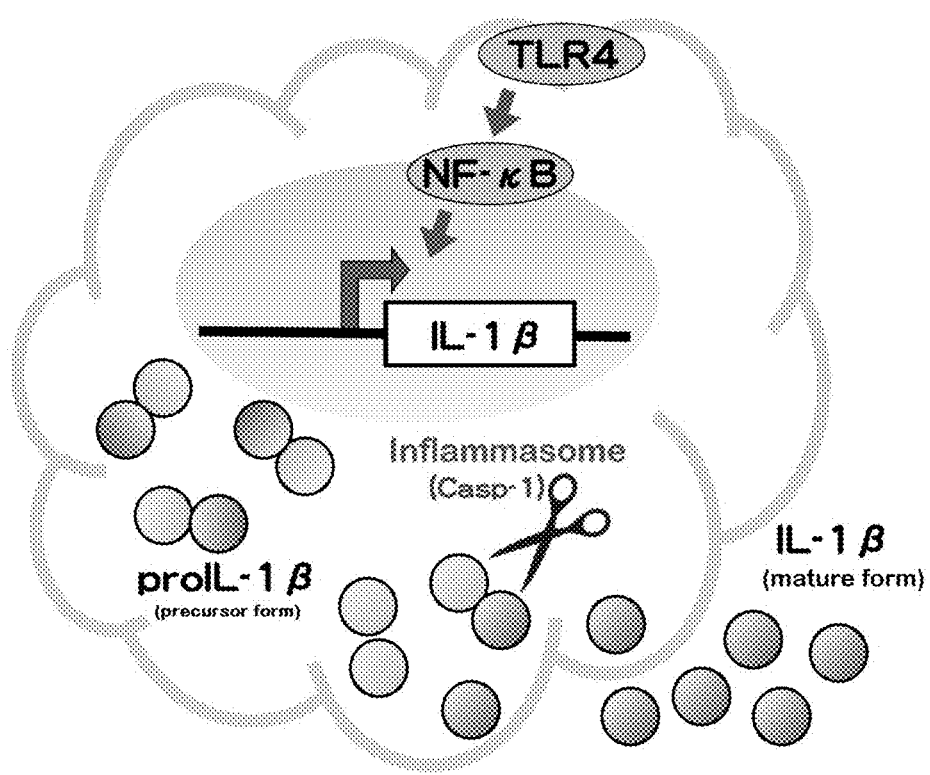
FIG. 2 shows the regulatory mechanism for IL-1β production and secretion.
Figure 3:
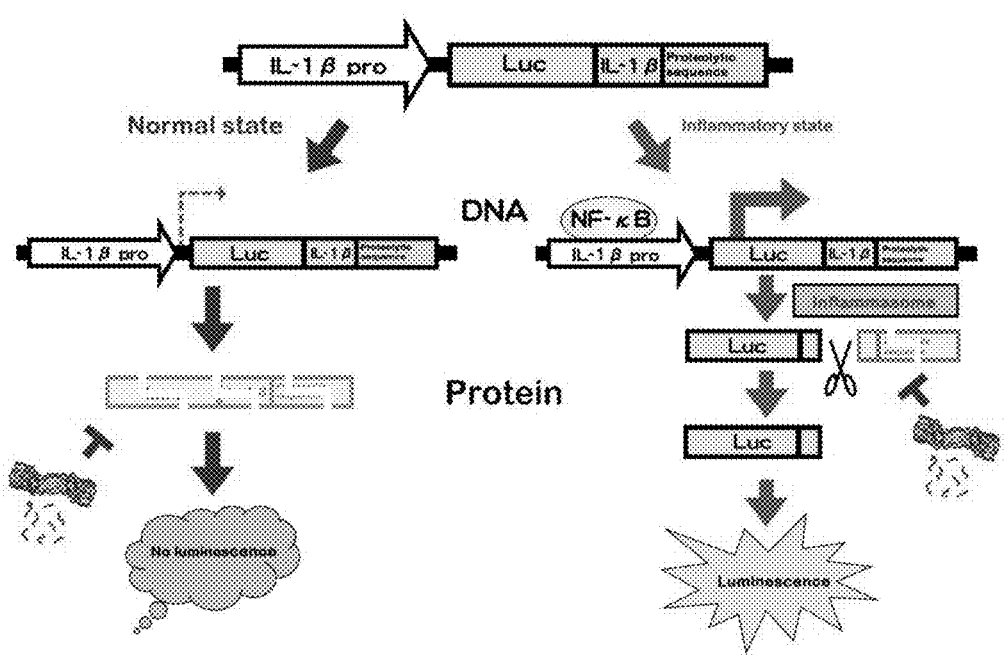
FIG. 3 shows the construction of an inflammation reporter system based on IL-1β.

FIG. 3 shows a schematic view of an inflammation reporter system in cells carrying such a gene construct. FIG.

3 illustrates an embodiment where IL-1β is given as an inflammatory cytokine and luciferase (Luc) is given as a reporter molecule. Of course, inflammatory cytokines and reporter molecules are not limited only to IL-1β and Luc shown in FIG. 3.

In FIG. 3, in the absence of inflammatory stimulation, the IL-1β gene promoter does not function and hence will not activate the expression of the reporter gene. Even if expression leakage occurs, inflammasomes also do not function in the absence of inflammatory stimulation, and the expressed fusion protein composed of a reporter molecule, a caspase recognition sequence and a proteolytic signal sequence will be preferentially degraded through the ubiquitin-proteasome system by the action of the proteolytic signal sequence.

On the other hand, in the presence of inflammatory stimulation, the promoter becomes functional by the action of transcription factor NF-κB to thereby activate the expression of the reporter gene, and the produced reporter molecule is cleaved from the proteolytic signal sequence upon inflammasome-induced activation of caspase, whereby the reporter molecule is stabilized by itself and luminescence signals (reporter signals) from the reporter protein can be detected at high levels. This detection result is visualized and can be confirmed from an image displayed on a monitor.

Figure 4:
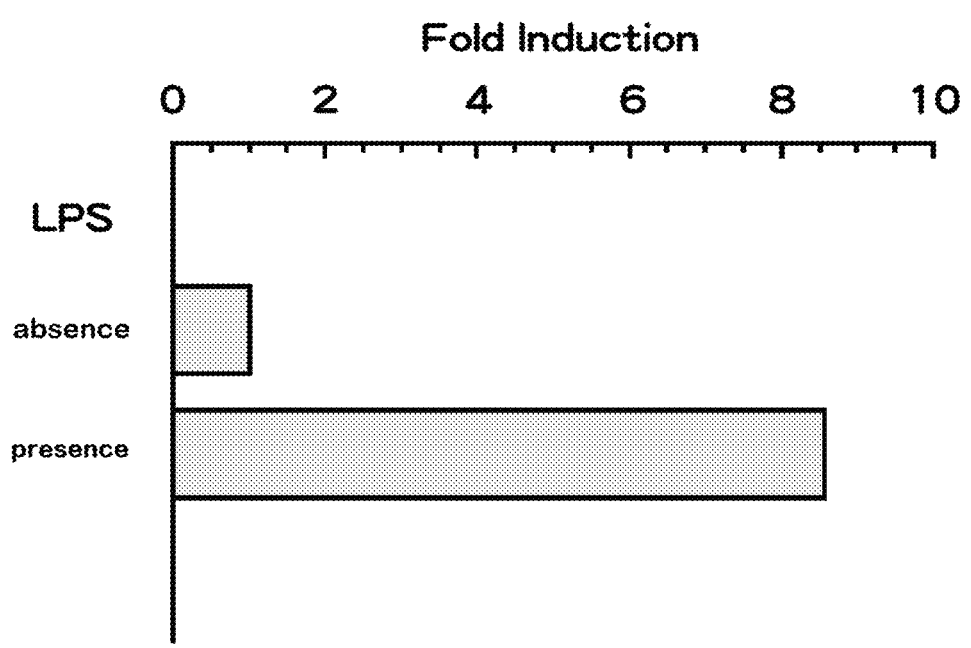
FIG. 4 shows reporter activity in RAW264 transiently transfected with a reporter gene. LPS used: SIGMA #L2654, concentration of use: 2 μg/ml

In one embodiment of the present invention, a gene vector configured to express a fusion protein composed of a reporter molecule, a caspase recognition sequence (which constitutes a portion of the amino acid sequence of IL-1β) and a proteolytic signal sequence under the control of a promoter for the IL-1β gene was transiently introduced into mouse-derived macrophage-like cell line RAW264. When LPS (lipopolysaccharide), which is a component constituting the *E. coli* cell membrane, is added to a culture of this cell line, a significant increase in reporter activity can be observed (FIG. 4).

In another embodiment, this gene vector was injected into a fertilized egg of the C57BL/6 strain at the pronucleus stage to thereby prepare a transgenic mouse. This transgenic mouse is exposed to inflammatory stimulation by being administered intraperitoneally with LPS, and changes in luminescence signals from luciferase are detected with a bioimaging analyzer immediately after administration and at 4 hours and 24 hours after administration. In all tissues of the body, luminescence dependent on inflammatory reaction can be observed (the Example section, FIG. 5).

Examples of a reporter protein (reporter molecule) available for use include luciferase, GFP (green fluorescent protein), DsRed (red fluorescent protein), LacZ (β-galactosidase) and so on. In addition, the gene vector may be in the form of plasmid DNA, viral vector or the like. However, the present invention is not limited to these examples.

Genes encoding these reporter proteins are known and are available from domestic and foreign bioreagent manufacturers, etc.

The term "proteolytic signal sequence" is intended to mean a sequence that is preferentially polyubiquitinated by the action of E3 ligase and thus becomes easily digested in proteasomes. Examples of a proteolytic signal sequence available for use in the present invention include a CL1 sequence, a PEST sequence and so on. Genes encoding these proteolytic signal sequences are known and are available from domestic and foreign bioreagent manufacturers, etc.

The transformant of the present invention may be obtained by introduction of the gene vector into a host.

The host into which the gene vector is introduced is not limited in any way and may be a unicellular organism, as exemplified by prokaryotic organisms (e.g., *E. coli*, lactic acid bacteria) and eukaryotic cells (e.g., yeast). For this purpose, it is also possible to use established cultured cell lines such as human-derived cell lines (e.g., Hela, HEK293) and mouse-derived cell lines (e.g., NIH3T3), or other animal cells. Techniques to ligate the above gene immediately downstream of a promoter are well known (Molecular Cloning: A Laboratory Manual (4th Edition), Cold Spring Harbor Laboratory Press (2012)). Introduction of the gene vector into the host may be accomplished by widely known techniques such as electroporation techniques, lipofection techniques with commercially available lipofection reagents, viral vector-mediated techniques and so on (see, e.g., Molecular Cloning mentioned above).

Transgenic non-human animals transfected with this reporter gene vector may be prepared from mice, rats, dogs, monkeys, goats or other animals, but are not limited to these non-human animals. Transgenic non-human animals may be prepared by injecting the gene vector DNA into fertilized eggs of these respective animals using a microinjector. Alternatively, embryonic stem cells (ES cells) or induced pluripotent stem cells (iPS cells) may be established by homologous recombination and then used to prepare transgenic animals. Microinjection and other techniques are all known techniques which can be easily carried out by those skilled in the art (see, e.g., Molecular Cloning mentioned above).

Transgenic non-human animals used in the present invention are not limited to whole animals, and it is also possible to use biomaterials derived from these transgenic non-human animals, including cells, organs, tissues, embryos, etc.

2. Screening Method

In the present invention, test substances (candidate substances) serving as candidates for anti-inflammatory substances are not limited in any way, and examples include peptides, proteins, DNAs, non-peptidic compounds, synthetic compounds, fermentation products, cell extracts, plant extracts and so on, which may be either novel compounds or known compounds. These test substances may form salts. Salts of test substances include those formed with physiologically acceptable acids (e.g., inorganic acids) or bases (e.g., organic acids), with physiologically acceptable acid addition salts being preferred. Test substances may be tested alone independently of each other or may be tested as a mixture (including a library). Examples of a library containing a plurality of test substances include synthetic compound libraries (e.g., combinatorial libraries), peptide libraries (e.g., combinatorial libraries), etc.

The present invention includes an embodiment where a transgenic non-human animal is administered with an inflammatory substance (exposed to inflammatory stimulation) to induce an inflammatory reaction and this animal is then contacted with a test substance to examine an inhibitory effect on the inflammatory reaction, and an embodiment where a transgenic non-human animal is contacted with a test substance and then administered with an inflammatory substance to induce an inflammatory reaction, followed by examination of an inhibitory effect on the inflammatory reaction in this animal. In either of these embodiments, a test substance found to have an inhibitory effect on the induced inflammatory reaction can be selected as a therapeutic or prophylactic agent for inflammatory diseases (e.g., infections, rheumatism, allergies), i.e., as an anti-inflammatory agent.

A transgenic non-human animal (test animal) to be administered with a test substance and a control animal are not limited in any way, although non-human animals of the same species are commonly used for this purpose. More preferably, animals of the same sex and of the same age are used as test and control animals.

In the case of using a transformant, the present invention includes an embodiment where the transformant is contacted with a test substance and this transformant is then contacted with an inflammatory substance to examine an inhibitory effect on the induced inflammatory reaction, and an embodiment where the transformant is contacted with an inflammatory substance to induce an inflammatory reaction and this transformant is then contacted with a test substance to examine an inhibitory effect on the inflammatory reaction.

For determination of whether or not an inflammatory reaction is inhibited, it is examined whether or not a reporter protein is detected as a luminescence signal upon inflammatory stimulation, and the resulting detection results are used to select an anti-inflammatory substance.

The term "contact" is intended to include, e.g., an embodiment where a test substance is administered to a non-human animal, an embodiment where a test substance is added to a transformant or a biomaterial, and an embodiment where cells are cultured in the presence of a test substance. To contact a test substance with transgenic non-human animals per se, the test substance may be inoculated into these animals through injection or other means. The embodiment where a test substance is added to a transformant or a biomaterial may be accomplished, e.g., by addition of the test substance to a cultured product of cells or by addition of the test substance to a tissue, an organ or the like. The term "cultured product" is intended to mean a cell, a cell culture or a cell extract. The expression "cultured in the presence of a test substance" is intended to mean that cells are cultured under conditions where the cells are contacted with a test substance, and contact of the test substance with the above cells or the like may be accomplished, e.g., by addition of the test substance to a cell culture medium or any type of buffer (e.g., HEPES buffer, phosphate buffer, phosphate-buffered physiological saline, Tris-HCl buffer) and incubation of the cells therein for a given period of time.

The concentration of a test substance to be added to a cultured product will vary depending on the type of compound (e.g., solubility, toxicity). For example, it is selected as appropriate within the range of 100 ng/ml to 10 µg/ml. The time required for incubation may be, for example, 4 to 48 hours.

3. Kit

The present invention provides a kit for detection of an inflammatory reaction or for screening of anti-inflammatory substances, which comprises a transformant or transgenic non-human animal transfected with a vector comprising a promoter for a gene encoding an inflammatory cytokine, a gene encoding a reporter protein, a gene encoding the inflammatory cytokine, and a gene encoding a proteolytic signal sequence.

In the case of using the transformant or transgenic non-human animal of the present invention as a detection reagent for inflammatory diseases or inflammatory reactions, the kit may comprise the above transformant or transgenic non-human animal together with other reagents, e.g., distilled water, buffering reagents, inflammation-inducing substances, instructions for use, etc.

EXAMPLES

The present invention will be further described in more detail by way of the following examples, which are not intended to limit the scope of the present invention.

Construction of Gene Vector

Figure 7:
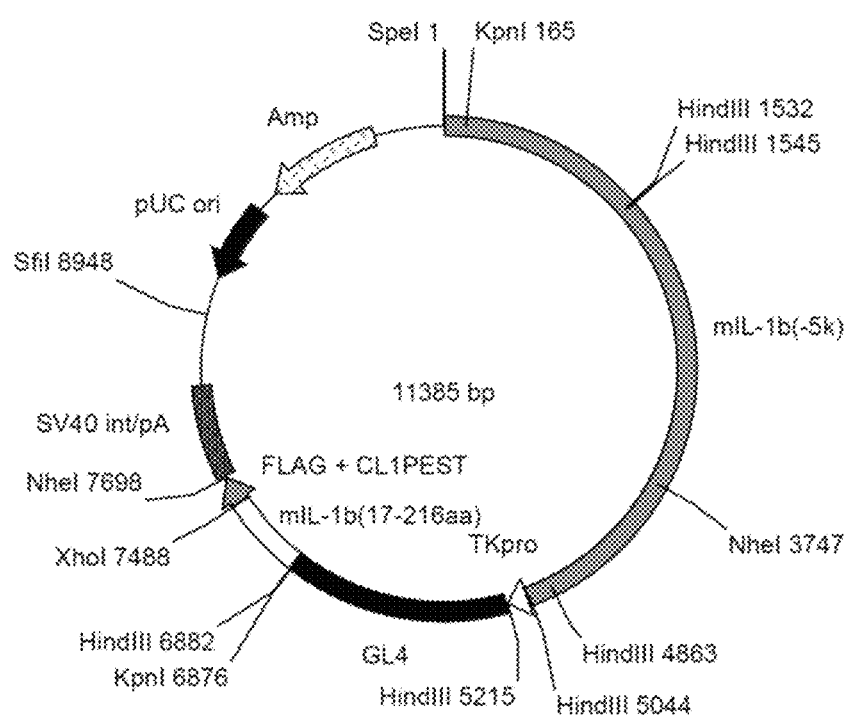
FIG. 7 shows the construction of the vector of the present invention.

A region of approximately 5 kbp upstream of the mouse-derived IL-1β gene was cloned from the genomic DNA extracted from mouse-derived cells. An HSV-derived TK gene promoter was fused immediately downstream of the cloned region, *Photinus pyralis*-derived modified luciferase (GL4, approximately 1.7 kbp) was ligated downstream of this fused promoter, a nucleotide sequence encoding a mouse-derived IL-1β partial sequence (17-216 aa) was further ligated downstream thereof, and a CL1 (derived from *Saccharomyces cerevisiae*)-PEST (derived from mouse) sequence and an SV40-derived polyA sequence were further ligated downstream thereof to thereby construct a vector (FIG. 7) (SEQ ID NO: 1).

Cloning of the IL-1β gene was accomplished as follows.

About a Region of Approximately 5 Kbp Upstream of the Mouse-Derived IL-1β Gene

The entire region was divided into 4 portions, and these portions were each cloned by PCR techniques. For each portion, the PCR kit used was Prime Star (Takara), the template DNA used was mouse ES cell-derived genomic DNA, and the reaction conditions were set to 35 cycles of 98° C. for 10 seconds, 55° C. for 5 seconds and 72° C. for 2 minutes. Different primers were used for each portion as shown below.

For the first portion

```
5-primer:
                                        (SEQ ID NO: 2)
aaaactagttcgtcttttgagaaagtcagggcag 3-primer:
                                        (SEQ ID NO: 3)
gaataggcatcgataaacaagattc
```

For the second portion

```
5-primer:
                                        (SEQ ID NO: 4)
gaatcttgtttatcgatgcctattc 3-primer:
                                        (SEQ ID NO: 5)
aaactcgaggcacatgcatgaagacgaatggcc
```

For the third portion

```
5-primer:
                                        (SEQ ID NO: 6)
aaactcgagatgcatgtgccttcctccaaatc 3-primer:
                                        (SEQ ID NO: 7)
gtaggagctagcccgggtgagtag
```

For the fourth portion

```
5-primer:
                                        (SEQ ID NO: 8)
aaaactagttcgtcttttgagaaagtcagggcaggaac 3-primer:
                                        (SEQ ID NO: 9)
aaaactagtcacaaggaagcttggctggagaggatc
```

It should be noted that a ClaI site, an EcoT22I site and a SmaI site were used for ligation of each portion.

About a Partial (17-216 Aa) Region of the Mouse-Derived IL-1β Gene

The entire region was cloned at once by PCR techniques. The PCR kit used was Prime Star (Takara), the template DNA used was a mouse placenta-derived reverse transcript, and the reaction conditions were set to 35 cycles of 98° C. for 10 seconds, 55° C. for 5 seconds and 72° C. for 1 minute.

The primers used were 5-primer: aaaggtaccgatgagaatgac-ctgttctttg (SEQ ID NO: 10) and 3-primer: aaactcgagaaac-cgttntccatcttcttc (SEQ ID NO: 11).

Transient Introduction into Cultured Cells

The gene vector constructed as above was transiently introduced into mouse-derived macrophage-like cell line RAW264.

For transfection, Effectene (Qiagen) was used, and the cells at 24 hours after transfection were collected and provided for experiments. To a culture of transiently expressing cells, LPS (Sigma #L2654) was added at a concentration of 2 μg/mL, and the amount of luciferase luminescence at 48 hours after addition was determined by being measured with a luminometer. For use as a control, an LPS-free group was provided. In addition, as a conventional reporter system detecting only IL-1β gene expression, a vector was prepared to have GL4 ligated downstream of a promoter for the IL-1β gene, and cells transfected with this vector were provided for the same test.

Figure 6:
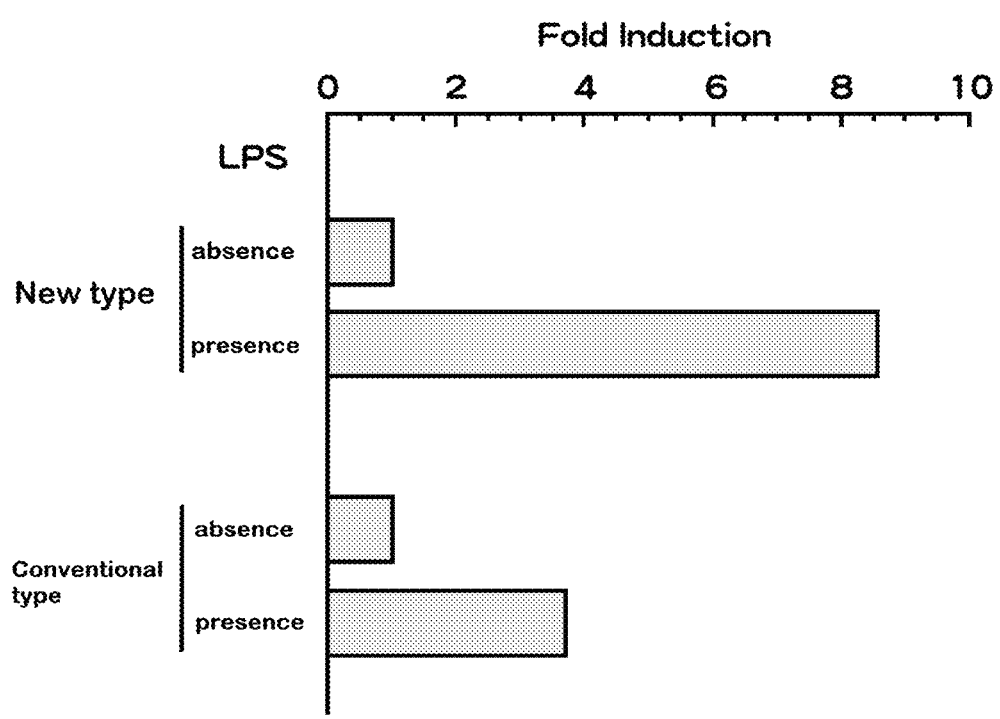
FIG. 6 shows reporter activity in RAW264 transiently transfected with a reporter gene. LPS used: SIGMA #L2654, concentration of use: 2 μg/ml, treatment time: 48 hours

As a result, the reporter signals shown in FIG. 6 were obtained. In the cells transfected either with the vector of the present invention or with the vector of conventional type, a significant increase in reporter signals was observed upon LPS stimulation. However, the vector of the present invention showed a 2-fold or more improvement in sensitivity when compared to the vector of conventional type.

Preparation of Transgenic Mouse

The excised and purified gene vector was injected into 200 fertilized eggs at the pronucleus stage which had been taken from mice of the C57BL/6 strain, thereby obtaining 71 pups. The genomic DNA extracted from the body tissue of each pup was used for genotype analysis to thereby obtain 18 founder mice having the gene vector inserted into their genome. Four founder mice were each crossed with a wild-type mouse of the C57BL/6 strain to produce F1 generation mice, which were then examined for reporter molecule reaction when intraperitoneally administered with LPS (Sigma #L2654).

Figure 8:
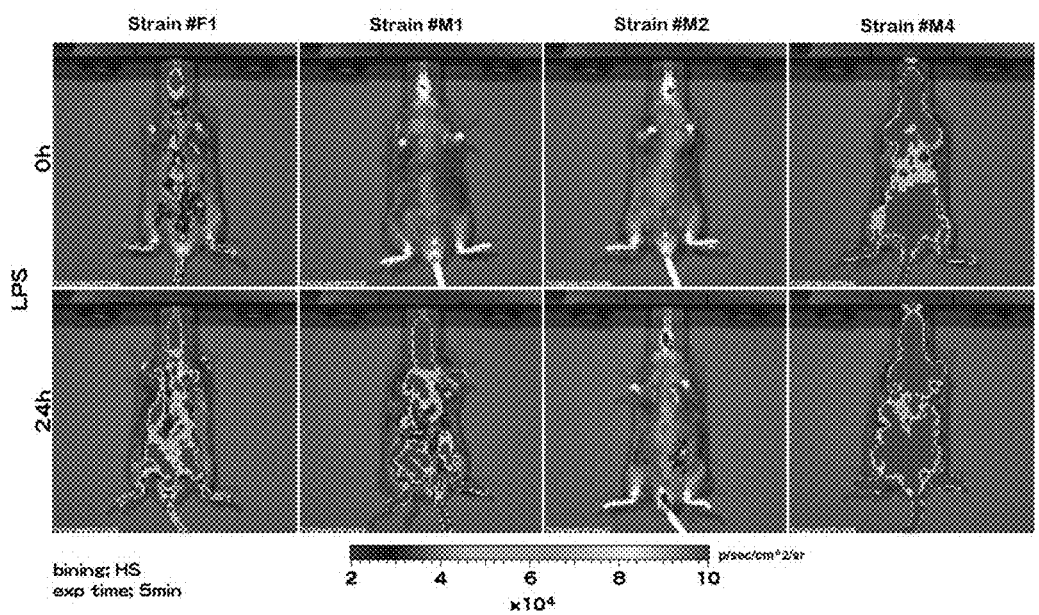
FIG. 8 shows the results compared for reporter signals before and after LPS stimulation among mouse strains.

As a result, the S/N ratio was highest in the mice of strain No. M1, and this strain was established as an inflammation reporter mouse (FIG. 8).

Visualization of Inflammatory Reactions Using Transgenic Mouse

Figure 5:
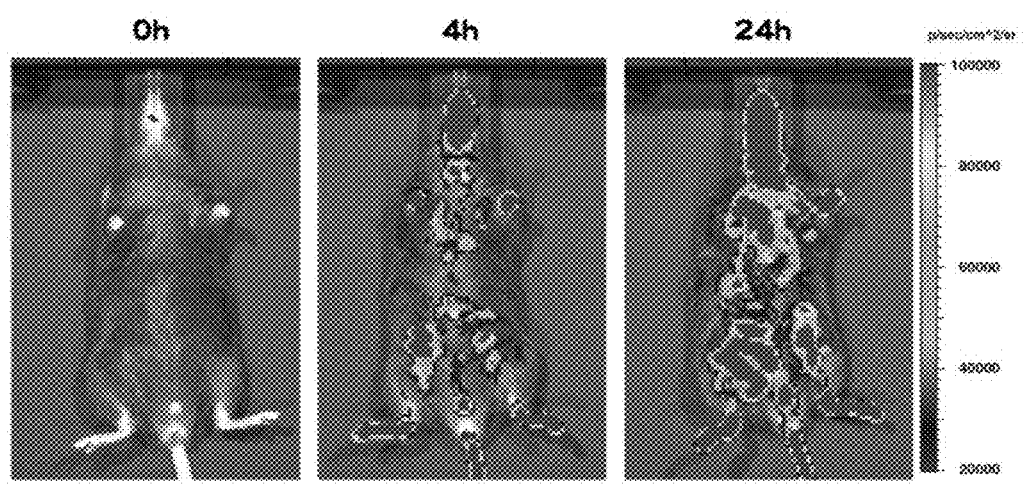
FIG. 5 shows signals emitted from LPS-stimulated inflammation reporter mice. LPS used: SIGMA #L2654, concentration of use: 3 to 4 μgig body weight

The inflammation reporter mouse thus established was intraperitoneally administered with LPS (Sigma #L2654) at a concentration of 3 mg/kg wt. At 0, 4 and 24 hours after administration, luciferase luminescence was observed with a bioimaging analyzer (IVIS). As a result, luminescence signals from luciferase were able to be captured from all tissues of the body (FIG. 5).

Sequence Listing Free Text

SEQ ID NOs: 1 to 11: synthetic DNAs

The invention claimed is:

1. A vector comprising an inflammatory cytokine promoter operably linked to a nucleotide sequence comprising a gene encoding a luciferase reporter protein, a gene encoding an inflammatory cytokine, wherein the inflammatory cytokine is a mouse-derived IL-1β partial sequence consisting of amino acids 17-216, and a gene encoding a proteolytic signal sequence,
   wherein the luciferase reporter protein, the inflammatory cytokine and the proteolytic signal sequence are configured as a fusion protein, wherein the inflammatory cytokine is N-terminal to the proteolytic signal sequence and C-terminal to the luciferase reporter protein, and
   wherein, in the presence of inflammatory stimulation, the inflammatory cytokine promoter becomes functional to thereby activate the expression of the nucleotide sequence and the inflammatory cytokine is cleavable by caspase-1 to separate the luciferase reporter protein from the proteolytic signal sequence while retaining luciferase activity.

2. A non-human transformant comprising the vector according to claim 1.

3. A transgenic non-human animal comprising in its genome the vector according to claim 1.

4. The transgenic non-human animal according to claim 3, wherein the non-human animal is a mouse.

5. The non-human transformant according to claim 2, wherein the reporter protein is detected as a luminescence signal upon inflammatory stimulation.

6. A method for detection of an inflammatory reaction, which comprises using the transformant according to claim 2 or the transgenic non-human animal according to claim 3 to detect an inflammatory reaction induced upon inflammatory stimulation in the transformant or in the transgenic non-human animal.

7. The method according to claim 6, wherein the gene encoding the inflammatory cytokine is expressed by transcription factor NF-κB induced during inflammatory reaction.

8. The method according to claim 6, wherein the reporter protein is detected as a luminescence signal upon inflammatory stimulation.

9. A method for screening of anti-inflammatory substances, which comprises bringing the transformant according to claim 2 or the transgenic non-human animal according to claim 3 into contact with candidate substances under inflammatory stimulation to select an anti-inflammatory substance on the basis of the presence or absence of an inflammatory reaction serving as an indicator.

10. A kit for detection of an inflammatory reaction or for screening of anti-inflammatory substances, which comprises the non-human transformant according to claim 2.

11. The vector of claim 1, wherein the promoter is an interleukin 1β inflammatory cytokine promoter, the reporter protein is *photinus pyralis* luciferase, and the proteolytic signal sequence comprises a CL1-PEST proteolytic signal sequence.

* * * * *

SEQUENCE LISTING

```
<160> NUMBER OF SEQ ID NOS: 11

<210> SEQ ID NO 1
<211> LENGTH: 8406
<212> TYPE: DNA
<213> ORGANISM: Artificial
<220> FEATURE:
<223> OTHER INFORMATION: Synthetic DNA

<400> SEQUENCE: 1
tcgtcttttg agaaagtcag ggcaggaaca caatcagggc agggacatgg aagcaggagc        60
tgatacaaag accatggaag attgctgctt actggcttgc ttcccttggc ttgctcagcc       120
tgttttctta tagaacccag aaccaccagc ccagggatgg taccatccac agtgagctgg       180
gccctctctt attaatcacc aattaataaa acgccctaca agtctaccta cagccagatc       240
ttacagaggc attttctcaa ttgagtctcc ctcctctctg atgactgtaa ctgtgtcatt       300
gacataaaac taatcagtac aactgacccc ttgccaactt gacacacaaa cacaccactt       360
tccttttttt aagatttatt tatttatata ttttatgtat atgggtgttt ttgtctgcat       420
gtactcctac acactagaag agtttattaa atcccatggg actactgtta cagatactgt       480
tagccaccat gtgggtgctg ggacttgaac tcaggacctc tggataagca gccagtgctc       540
taaattgctg agctcaaggc ccaacttatc actttttaat tagaaccttt cttttctcat       600
ttatccccaa gatgttatgt taatatttat atcacaatat aaaacattaa caacttaaag       660
gtcccacaat cctcacaaat tcaaatacat taaaagttct ctctctttaa aataatcaat       720
ctcttttaaa attcagtctc tcaactttgg acttctgtaa aatcaaaaat aaattatatt       780
tcaagagaga agaactaggt caaaatcgca atcaaagcaa agcaaaacca aactccaaaa       840
atgtaaatag tgcatgttcc aacgtcaaag atgcactcaa gatcttctgg gatcctctaa       900
```

-continued

```
ggggcttgag ttacttctgc agctcagccc tttgtagcac aaacagcttg tcttttagga      960
tttggctggc tccactccac tgctgctgct gttcttgatg gtcatcccat ggtacttgca     1020
tctccaaaat gctggggtct tctgctgcaa ctgggctgga cttataccag tactctcctg     1080
ggctctcttc atggtgacaa gcctcaactt ctctgtatga ccctttcaat cctgggcctt     1140
cagctgccac tgaggctgta ttgtcagtgc aagactcag ctgctcttcc atgaaccagt      1200
gtcacctggg tggctcttcc acaggaccaa atttggctgc cagtggagaa atacaacttt     1260
ggccatctct ggaaaacagc ttctgtgtgc tctcagaaaa cacttcccag aagatttcac     1320
ctcaataatg ctggactttt cttagtcact gctaatttct cagctccagc tcaccagcac     1380
tgagtatcta agcaaagcaa aggtttcatt tttagtggtt ctggaatctt gtttatcgat     1440
gcctattctt cagccccagc taatgagata ttatgttatc acggaatctt aattcaatat     1500
aacaaatggc cctgaagaag tctttaagct tccttctgaa gcttcacaag tcaggcctcc     1560
atctttgtgt tgccctcaac gtccctatct tccaagttcc taggaacagc tcaccaagaa     1620
ttgaccactc tatgggtttt cttgtacaaa gtccttccaa acaatatgc tcaggtctgt      1680
cacagtcatg tcacagtaaa tcttggtgcc aattcatttt catttaggtt actattacta     1740
taatgaaact ccatgatcaa agcaacttgg ggaggaaagg atgtattctg cttacatttc     1800
cacatcacag tttatcatca aaggaagtca ggacaggaac tcaagcaagg caggaacctg     1860
gaaccaggag ctgatgcagc gatcatggag ggatgctgct cactggcttg ctcctcatgg     1920
cttgtcaacc tactttctta tagaacccag gaccaccagc ccagggatgg caccaccccac    1980
aacaggctga tttctcccca gtaaatacc aattaataaa atttcctaca ggcttgccta      2040
cagacagatc ttttgatgt attttgtcag ttaaggctcc cttctctctg atgattctag      2100
cttgtgtcta gttgacataa aactaaccag gacagaaaag atgagaggga agaacagac      2160
ccctaaggcc tgtgctaagt cgtcaactta aggaataaga caaggtctgg agaaagtaat     2220
gaggacagtc attgcttagc tctgttctga gcaagaggat aagtaaagaa gatgtagaac     2280
acatacatca actgggcctg ggagctcgtg cctgtaatct cagtccttgg gagacaaatg     2340
caggagaatt gtcatgtact tgaagccagt ctgggctgca cagtagtcat ggttatcaca     2400
gcaatagaaa gtaagtaaaa caggtagcaa ggcactttca gctttgaaga aatgcctgcc     2460
tccatcttgg aggaatgaga tgtcagaaca gagggaacct tacagcttaa aagtgctgag     2520
tgagtcaaga gctgaaaagt tccccaaaag ctagagtgcc cgtcaccatc ctggctttgc     2580
cgacttcctc ttttgctttg ttcatttcct ttgccaacat catcatcagt atcgtcatca     2640
ctatgccaca cccccagcat aacaatttct atagtgagtt atttcttcta ctcattgggg     2700
accaaaaagg aagtgtggtc tgagagacag ggtttgatat acatgttgtg caacttgcct     2760
gctctataac gacaagggga ggaaatttgg agcccaagtc acagggccag gatgaggttt     2820
gatagaacaa tagagtacca gaggcattgc ccagtagttc caaaatctcc ctctagaagc     2880
aaaagaatca tcaaccagat cattgcctcc tcccagacaa acctcctccc atctcttcat     2940
ctcttactca cgattaaatg gccattcgtc ttcatgcatg tgccttcctc caaatcctcc     3000
cagacaacca ctcctctcag gcatcagctc aagggtttag gagtgttata actagcagat     3060
ggtgaagaag attctgtaac tagactgagc tcaaggctcc tgaaaaatca tccagggaga     3120
agggacttgg agctgacact caggccccta gttaccttc tctgtcccct ggttttcacc      3180
atccctggtt caactcacat cagcagacca aaggagtctc caataatctc tgtcaggaca     3240
```

```
gcccataaaa tcatcagacc ttccagccct gcacacaggc tctgaggaag gtgttagtcc    3300
ctccaggcat agtttgaaat gtggaccctg tgaaggcaga acagaaaaat gaaccagatg    3360
gcccagacag gacctctgga ttgtctgcag aactagataa tacatcttat aagaccttag    3420
tgctgagaac tgaccattgc tcaccaaact caaaagcaac tgagaccctg aaccatcttc    3480
agatttcaaa tcaaacatat agctggtcaa aggcaggatt cttctgtttg ccttcctgaa    3540
atcgagatgc tgtgaaccaa attaggcaaa agaaggctgc ctagtaagta aaccttgttt    3600
catagtagag ccttgtctat tcctccttcc aattctgtct gtctatttcc cttcagtgct    3660
gcagaataag ctcagtaacc aaaacatact aggtacaaac tcatctgaat gaacacattg    3720
ccaaattcct actcacccgg gctagctcct actgcctgca tccatctgcc aggcactgtg    3780
gagacctggc tctaatggag tccacagact ctctgagggc tcagcaaagg agttaggttt    3840
ccactgagga ttctactata ctgtagatgt gcccaagaga ctgtatgcag cattcatatg    3900
gcctggttgc tcattccatc caagcaagaa gagctcccct gggtaggctc cctgggctct    3960
ctgagttagc agtctagtga tgcttgatat ggccaagaga cttggtctcc ccagatctta    4020
tagaaacaag aattttccaa aacaattttt taggcaaaga ctatctcttc acttttaag    4080 atggactgtg ctcatgaaca ggcagatgcc tcgttcacca cctttgcact gtgcaactta    4140
attcaggctc attctgctga tcacctagca ctgatatggt ttcaacatga gactggctat    4200
ggtattataa gtaccctggc agggcaggaa agcaggagtg ggtgggtgag tgggggagca    4260
tcctcataga ggcaggggag ggggagagga taggggtttt ccggagggga gacctggaaa    4320
agggataaca tttgaaatgt aaataaagaa aatatccaat aaaagaaaaa aataagcacc    4380
ctggcattat cagactgcat aggcttgctt ccagagttcc ctgaccctat gataagtcta    4440
cactgatacc tgcatactgt gtgtgccctg acccacacaa ggaagtgcgt gtctctccag    4500
aagcccctgc taacacagtt gatggagagc acagaagcac catccagtta ccaaactcca    4560
actgcaaagc tccctcagct taagcacaag gaggcgagag aggtgacaca cttctgggtg    4620
tgcatctacg tgcctacctt tgttccgcac atcctgactt aaaatgtaca gctaacccag    4680
gaaaacccaa tatttttaat attgacacca tctgcacaat tgtccagggg gaaataatgc    4740
ccatttccac cacgatgaca cacttgcgaa tgtgtcacta tctgccaccc cttgacttcc    4800
agggattaga aattatttca gggtagcaat agcctcttcc cctaagaatt cccatcaagc    4860
ttctcccccc tcccccaccc ttcagttttg ttgtgaaatc agttaaccca agggaaaatt    4920
tcacagctct tcacttctgc tttttaggac tataaaacaa gggagggaaa acaagttgga    4980
caacaaaccc tgcagtggtt cgaggcctaa taggctcatc tgggatcctc tccagccaag    5040
cttccttgtg actagaggcc ccgcccagcg tcttgtcatt ggcgaattcg aacacgcaga    5100
tgcagtcggg gcggcgcggt ccgaggtcca cttcgcatat taaggtgacg cgtgtggcct    5160
cgaacaccga gcgaccctgc agcgaccngc ttaacagcgt caacagcgaa gcttccacca    5220
tggaagatgc caaaaacatt aagaagggcc cagcgccatt ctacccactc gaagacggga    5280
ccgccggcga gcagctgcac aaagccatga gcgctacgc cctggtgccc ggcaccatcg    5340
cctttaccga cgcacatatc gaggtggaca ttacctacgc cgagtacttc gagatgagcg    5400
ttcggctggc agaagctatg aagcgctatg gcctgaatac aaaccatcgg atcgtggtgt    5460
gcagcgagaa tagcttgcag ttcttcatgc ccgtgttggg tgccctgttc atcggtgtgg    5520
ctgtggcccc agctaacgac atctacaacg agcgcgagct gctgaacagc atgggcatca    5580
gccagcccac cgtcgtattc gtgagcaaga aagggctgca aaagatcctc aacgtgcaaa    5640
```

```
agaagctacc gatcatacaa aagatcatca tcatggatag caagaccgac taccagggct   5700
tccaaagcat gtacaccttc gtgacttccc atttgccacc cggcttcaac gagtacgact   5760
tcgtgcccga gagcttcgac cgggacaaaa ccatcgccct gatcatgaac agtagtggca   5820
gtaccggatt gcccaagggc gtagccctac cgcaccgcac cgcttgtgtc cgattcagtc   5880
atgcccgcga ccccatcttc ggcaaccaga tcatccccga caccgctatc ctcagcgtgg   5940
tgccatttca ccacggcttc ggcatgttca ccacgctggg ctacttgatc tgcggctttc   6000
gggtcgtgct catgtaccgc ttcgaggagg agctattctt gcgcagcttg caagactata   6060
agattcaatc tgccctgctg gtgcccacac tatttagctt cttcgctaag agcactctca   6120
tcgacaagta cgacctaagc aacttgcacg agatcgccag cggcggggcg ccgctcagca   6180
aggaggtagg tgaggccgtg gccaaacgct tccacctacc aggcatccgc cagggctacg   6240
gcctgacaga aacaaccagc gccattctga tcacccccga aggggacgac aagcctggcg   6300
cagtaggcaa ggtggtgccc ttcttcgagg ctaaggtggt ggacttggac accggtaaga   6360
cactgggtgt gaaccagcgc ggcgagctgt gcgtccgtgg ccccatgatc atgagcggct   6420
acgttaacaa ccccgaggct acaaacgctc tcatcgacaa ggacggctgg ctgcacagcg   6480
gcgacatcgc ctactgggac gaggacgagc acttcttcat cgtggaccgg ctgaagagcc   6540
tgatcaaata caagggctac caggtagccc cagccgaact ggagagcatc ctgctgcaac   6600
accccaacat cttcgacgcc ggggtcgccg gcctgcccga cgacgatgcc ggcgagctgc   6660
ccgccgcagt cgtcgtgctg gaacacggta aaaccatgac cgagaaggag atcgtggact   6720
atgtggccag ccaggttaca accgccaaga agctgcgcgg tggtgttgtg ttcgtggacg   6780
aggtgcctaa aggactgacc ggcaagttgg acgcccgcaa gatccgcgag attctcatta   6840
aggccaagaa gggcggcaag atcgccgtgg gtaccaagct tgatgagaat gacctgttct   6900
ttgaagttga cggaccccaa aagatgaagg gctgcttcca aacctttgac ctgggctgtc   6960
ctgatgagag catccagctt caaatctcgc agcagcacat caacaagagc ttcaggcagg   7020
cagtatcact cattgtggct gtggagaagc tgtggcagtc acctgtgtct ttcccgtgga   7080
ccttccagga tgaggacatg agcaccttct tttccttcat ctttgaagaa gagcccatcc   7140
tctgtgactc atgggatgat gatgataacc tgctggtgtg tgacgttccc attagacaac   7200
tgcactacag gctccgagat gaacaacaaa aaagcctcgt gctgtcggac ccatatgagc   7260
tgaaagctct ccacctcaat ggacagaata tcaaccaaca agtgatattc tccatgagct   7320
ttgtacaagg agaaccaagc aacgacaaaa tacctgtggc cttgggcctc aaaggaagaa   7380
atctatacct gtcctgtgta atgaaagacg gcacacccac cctgcagctg gagagtgtgg   7440
atcccaagca atacccaaag aagaagatgg aaaaacggtt tctcgaggac tacaaggatg   7500
acgatgacaa gaattctgct tgcaagaact ggttcagtag cttaagccac tttgtgatcc   7560
accttaacag ccacggcttc cctcccgagg tggaggagca ggccgccggc accctgccca   7620
tgagctgcgc ccaggagagc ggcatggata gacaccctgc tgcttgcgcc agcgccagga   7680
tcaacgtcta agctagctag gtagctagag gatctttgtg aaggaacctt acttctgtgg   7740
tgtgacataa ttggacaaac tacctacaga gatttaaagc tctaaggtaa atataaaatt   7800
tttaagtgta taatgtgtta aactactgat tctaattgtt tgtgtatttt agattccaac   7860
ctatggaact gatgaatggg agcagtggtg gaatgccttt aatgaggaaa acctgttttg   7920
ctcagaagaa atgccatcta gtgatgatga ggctactgct gactctcaac attctactcc   7980
```

-continued

```
tccaaaaaag aagagaaagg tagaagaccc caaggacttt ccttcagaat tgctaagttt    8040
tttgagtcat gctgtgttta gtaatagaac tcttgcttgc tttgctattt acaccacaaa    8100
ggaaaaagct gcactgctat acaagaaaat tatggaaaaa tatttgatgt atagtgcctt    8160
gactagagat cataatcagc cataccacat ttgtagaggt tttacttgct ttaaaaaacc    8220
tcccacacct cccctgaac ctgaaacata aatgaatgc aattgttgtt gttaacttgt     8280
ttattgcagc ttataatggt tacaaataaa gcaatagcat cacaaatttc acaaataaag    8340 cattttttc actgcattct agttgtggtt tgtccaaact catcaatgta tcttatcatg    8400
tctgga                                                             8406

<210> SEQ ID NO 2
<211> LENGTH: 34
<212> TYPE: DNA
<213> ORGANISM: Artificial
<220> FEATURE:
<223> OTHER INFORMATION: Synthetic DNA

<400> SEQUENCE: 2
aaaactagtt cgtcttttga gaaagtcagg gcag                               34

<210> SEQ ID NO 3
<211> LENGTH: 25
<212> TYPE: DNA
<213> ORGANISM: Artificial
<220> FEATURE:
<223> OTHER INFORMATION: Synthetic DNA

<400> SEQUENCE: 3
gaataggcat cgataaacaa gattc                                         25

<210> SEQ ID NO 4
<211> LENGTH: 25
<212> TYPE: DNA
<213> ORGANISM: Artificial
<220> FEATURE:
<223> OTHER INFORMATION: Synthetic DNA

<400> SEQUENCE: 4
gaatcttgtt tatcgatgcc tattc                                         25

<210> SEQ ID NO 5
<211> LENGTH: 33
<212> TYPE: DNA
<213> ORGANISM: Artificial
<220> FEATURE:
<223> OTHER INFORMATION: Synthetic DNA

<400> SEQUENCE: 5
aaactcgagg cacatgcatg aagacgaatg gcc                                33

<210> SEQ ID NO 6
<211> LENGTH: 32
<212> TYPE: DNA
<213> ORGANISM: Artificial
<220> FEATURE:
<223> OTHER INFORMATION: Synthetic DNA

<400> SEQUENCE: 6
aaactcgaga tgcatgtgcc ttcctccaaa tc                                 32

<210> SEQ ID NO 7
<211> LENGTH: 24
```

```
<212> TYPE: DNA
<213> ORGANISM: Artificial
<220> FEATURE:
<223> OTHER INFORMATION: Synthetic DNA

<400> SEQUENCE: 7
gtaggagcta gcccgggtga gtag                                          24

<210> SEQ ID NO 8
<211> LENGTH: 38
<212> TYPE: DNA
<213> ORGANISM: Artificial
<220> FEATURE:
<223> OTHER INFORMATION: Synthetic DNA

<400> SEQUENCE: 8
aaaactagtt cgtcttttga gaaagtcagg gcaggaac                           38

<210> SEQ ID NO 9
<211> LENGTH: 36
<212> TYPE: DNA
<213> ORGANISM: Artificial
<220> FEATURE:
<223> OTHER INFORMATION: Synthetic DNA

<400> SEQUENCE: 9
aaaactagtc acaaggaagc ttggctggag aggatc                             36

<210> SEQ ID NO 10
<211> LENGTH: 31
<212> TYPE: DNA
<213> ORGANISM: Artificial
<220> FEATURE:
<223> OTHER INFORMATION: Synthetic DNA

<400> SEQUENCE: 10
aaaggtaccg atgagaatga cctgttcttt g                                  31

<210> SEQ ID NO 11
<211> LENGTH: 31
<212> TYPE: DNA
<213> ORGANISM: Artificial
<220> FEATURE:
<223> OTHER INFORMATION: Synthetic DNA

<400> SEQUENCE: 11
aaactcgaga aaccgttttt ccatcttctt c                                  31
```